(12) United States Patent
Sweat

(10) Patent No.: US 7,828,709 B2
(45) Date of Patent: Nov. 9, 2010

(54) BLOOD PROCESSING APPARATUS WITH INCIPIENT SPILL-OVER DETECTION

(75) Inventor: William Sweat, Lakewood, CO (US)

(73) Assignee: CaridianBCT, Inc., Lakewood, CO (US)

( * ) Notice: Subject to any disclaimer, the term of this patent is extended or adjusted under 35 U.S.C. 154(b) by 294 days.

(21) Appl. No.: 12/241,846

(22) Filed: Sep. 30, 2008

(65) Prior Publication Data

US 2010/0078392 A1 Apr. 1, 2010

(51) Int. Cl.
*B01D 21/26* (2006.01)
(52) U.S. Cl. .............................. 494/37; 494/10; 210/745
(58) Field of Classification Search .................. 494/10, 494/37, 45; 210/87, 745
See application file for complete search history.

(56) References Cited

U.S. PATENT DOCUMENTS

| | | | |
|---|---|---|---|
| 4,094,461 A | 6/1978 | Kellogg et al. | |
| 4,425,112 A | 1/1984 | Ito | |
| 4,647,279 A | 3/1987 | Mulzet et al. | |
| 5,722,926 A | 3/1998 | Hlavinka | |
| 5,951,877 A | 9/1999 | Langley et al. | |
| 6,053,856 A | 4/2000 | Hlavinka | |
| 6,334,842 B1 | 1/2002 | Hlavinka et al. | |
| 7,327,443 B2 | 2/2008 | Scibona et al. | |
| 7,422,693 B2 | 9/2008 | Carter et al. | |
| 2005/0051466 A1* | 3/2005 | Carter et al. | 494/10 |
| 2006/0032817 A1* | 2/2006 | Westberg et al. | 494/37 |
| 2007/0102374 A1 | 5/2007 | Kolenbrander | |
| 2008/0041772 A1 | 2/2008 | Sweat et al. | |

* cited by examiner

*Primary Examiner*—Walter D Griffin
*Assistant Examiner*—Timothy Cleveland
(74) *Attorney, Agent, or Firm*—John R. Merkling; Edna M. O'Connor; Laura Butterfield Arciniegas

(57) ABSTRACT

A density centrifuge blood processing system comprising a separation chamber rotating about a central rotation axis, the separation chamber being coupled to an elutriation chamber, a first detector for the separation chamber to detect light from an observation region, a computational apparatus distinguishing at least two regions in the observation region and distinguishing incipient spill over of cellular components out of the elutriation chamber as a function of light intensity received from the at least two regions in the separation chamber, and a controller regulating speed of at least one pump or of the separation chamber in response to signals from the computational apparatus to avoid spill over.

14 Claims, 11 Drawing Sheets

US 7,828,709 B2

BLOOD PROCESSING APPARATUS WITH INCIPIENT SPILL-OVER DETECTION

FIELD OF THE INVENTION

The present invention relates to an apparatus and method for separating particles or components of a fluid. The invention has particular advantages in connection with separating blood components, such as white blood cells and platelets.

DESCRIPTION OF THE RELATED ART

In the medical field, it is often necessary to separate blood into components. Whole blood consists of various liquid components and particle components. The liquid portion of blood is largely made up of plasma. The particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle components are related according to size, in order of decreasing size, as follows: white blood cells, red blood cells, and platelets.

Typically, donated platelets are separated or harvested from other blood components using a centrifuge. White cells or other selected components may also be harvested. The centrifuge rotates a blood separation vessel to separate components within the vessel or reservoir using centrifugal force. In use, blood enters the separation vessel while it is rotating rapidly and centrifugal force stratifies the blood components, so that particular components may be separately removed. Components are removed through ports arranged within stratified layers of blood components.

White blood cells and platelets in plasma form a medium density stratified layer or "buffy coat". Because typical centrifuge collection processes are unable to consistently and satisfactorily separate white blood cells from platelets in the buffy coat, other processes have been added to improve results. One separation process is one known as centrifugal elutriation. In one common form of elutriation, a cell batch is introduced into a flow of liquid elutriation buffer, which carries the cell batch in suspension into a funnel-shaped chamber located on a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber. It is important to prevent cells being accumulated in the elutriation chamber from spilling over into collection bags prematurely, as this contaminates the blood component being collected, such as plasma, with unwanted components, such as platelets or white blood cells.

The elutriation chamber usually has at least a first frustroconical segment adjacent a fluid inlet and extending radially inward therefrom. The walls of the first frustro-conical segment may be linear, curved, or stepped, for example. The apparatus has at least one pump controlling a rate of fluid flow through the elutriation chamber.

Additional technology related to this application is disclosed in, for example, U.S. Pat. No. 5,722,926, issued Mar. 3, 1998; U.S. Pat. No. 5,951,877, issued Sep. 14, 1999; U.S. Pat. No. 6,053,856, issued Apr. 25, 2000; U.S. Pat. No. 6,334,842, issued Jan. 1, 2002; U.S. patent application Ser. No. 10/905,353, filed Dec. 29, 2004; U.S. patent application Ser. No. 11/163,969, filed Nov. 4, 2005 and in particular U.S. Pat. No. 7,422,693, issued Sep. 9, 2008.

SUMMARY OF THE INVENTION

The present invention is directed to detecting conditions indicating incipient spill over of cellular material out of separation chamber through either an outflow tube or an elutriation chamber and preventing such spill over by altering flow conditions in the blood component separation apparatus. The blood component separation apparatus has a rotor for centrifugally separating blood into phases such as red blood cells, white blood cells or buffy coat, or plasma. A camera monitors a separation chamber and image processing determines the location of fluid boundaries between phases. The apparatus controls the position of the boundaries by adjusting the speed of pumps or the rotor or both.

In the apparatus described herein, fluid flow in a blood separation chamber in a centrifugal separation device is initially controlled by optical sensing of two regions in the separation chamber. Interface position may be controlled by optical sensing of a two-dimensional view of the interface in the separation chamber in an area adjacent an outflow port or ports. Gross adjustments, that is, relatively large changes in the location of the interface or interfaces are best controlled by the observation of the interface. Thus in transient states, such as the initial setup of flow conditions, interface position sensing can be effective. Fluid flow may also be controlled in response to the optical intensity (light or dark) of the fluid in the outflow tube. This optical intensity correlates to presence of certain blood components such as red blood cells. Fine adjustments, that is, relatively small changes in the location of the interface are best controlled by sensing the optical intensity in the outflow tube. In steady state conditions, such as the extraction of a blood component through the outflow tube, outflow intensity sensing is more effective.

After steady state conditions have been established, and particularly when plasma is being removed from the separation chamber through an outflow tube or when platelets and white blood cells are being captured in an elutriation chamber, the apparatus of the present invention detects conditions indicating potential or incipient spill over of platelets or white blood cells out of the separation chamber into either the outflow tube or the elutriation chamber. The apparatus of the invention detects such conditions by monitoring the separation chamber, not the tube into the elutriation chamber. Flow conditions in the separation chamber can be changed in response to such detected changes to avoid actual spill over of unwanted cells, which would contaminate a collected blood product, such as plasma.

It is an object of the present invention, therefore, to provide a centrifuge blood processing system for separating fluid components comprising a separation chamber rotating about a central rotation axis, at least one pump regulating fluid flow in the separation chamber; a detector in optical communication with the separation chamber to receive and detect intensity of the light from the two regions; a computational apparatus comparing intensities in the two regions and further distinguishing incipient spill over changes in fluid flow in the separation chamber as a function of light intensity received from the two regions; and a controller regulating the speed of the pump or the speed of said separation chamber in response to signals from the computational apparatus to avoid spill over of cellular components from the separation chamber. The regions may comprise a plasma region and a red blood cell region, the regions being placed such that, under normal circumstances, the plasma region observes primarily plasma and the red blood cell region observes primarily red blood cells.

It is also an object of the invention to provide centrifuge blood processing having a computational apparatus that computes an intensity ratio of intensity of the plasma region to intensity of the red blood cell region, and a maximum intensity ratio. The computational apparatus declares a condition of incipient spill over whenever the intensity ratio falls below a pre-determined portion of the maximum intensity ratio.

A further object of the invention is to provide a centrifuge blood processing system wherein the computational apparatus declares an armed condition whenever the intensity ratio exceeds a pre-determined value and to record the maximum intensity ratio only after an armed condition has been declared.

Another object of the invention is to provide a centrifuge blood processing system wherein a detector in optical communication with a separation chamber receives and detects intensity of light from a buffy coat region, the buffy coat region being placed such that, under normal circumstances, the buffy coat region observes buffy coat, and wherein the computational apparatus declares a condition of incipient spill over whenever the intensity from said buffy coat region falls by a predetermined amount.

It is to be understood that both the foregoing general description and the following detailed description are exemplary, and are intended to provide further explanation of the invention as claimed.

DETAILED DESCRIPTION

The present invention preferably comprises a blood processing apparatus having a camera control system, as disclosed in U.S. Pat. No. 7,422,693 and in U.S. patent application Ser. Nos. 10/905,353 and 11/774,073. It may also be practiced with a TRIMA® blood component centrifuge manufactured by CaridianBCT, Inc. of Colorado or, alternatively, with a COBE® SPECTRA single-stage blood component centrifuge also manufactured by CaridianBCT, Inc. Both the TRIMA and the SPECTRA centrifuges incorporate a one-omega/two-omega sealless tubing connection as disclosed in U.S. Pat. No. 4,425,112 to Ito. The SPECTRA centrifuge also uses a single-stage blood component separation channel substantially as disclosed in U.S. Pat. No. 4,094,461 to Kellogg et al. and U.S. Pat. No. 4,647,279 to Mulzet et al. The invention could also be practiced with a TRIMA or TRIMA ACCEL® centrifugal separation system or other types of centrifugal separator. The method of the invention is described in connection with the aforementioned blood processing apparatus and camera control system for purposes of discussion only, and this is not intended to limit the invention in any sense.

Figure 1:
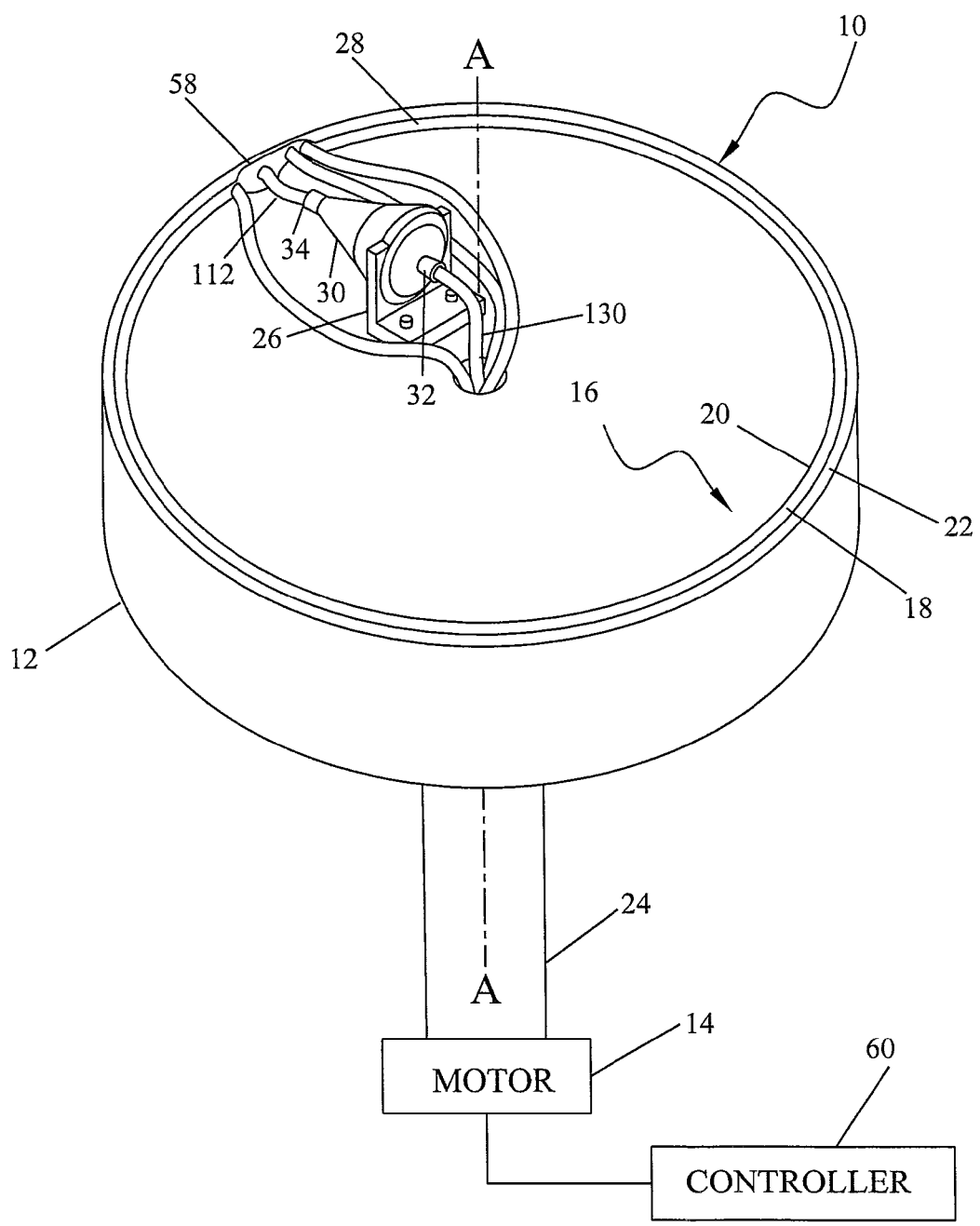
FIG. 1 is a schematic view of a blood processing centrifuge apparatus including an elutriation chamber.

As embodied herein and illustrated in FIG. 1, a centrifuge apparatus 10 has a centrifuge rotor 12 coupled to a motor 14 so that the centrifuge rotor 12 rotates about its axis of rotation A-A. The motor 14 is coupled to the rotor 12 through a shaft 24 connected to the rotor 12. Alternately, the shaft 24 may be coupled to the rotor 12 and the motor 14 through a gearing transmission (not shown).

The rotor 12 has a retainer 16 including a passageway or annular groove 18. The groove 18 opens upward to receive a separation vessel 28, shown in pertinent part in FIG. 4. As shown, the groove 18 completely surrounds the rotor's axis of rotation A-A and is bounded by an inner wall 20 and an outer wall 22 spaced apart from one another to define the groove 18. Although the groove 18 shown in FIG. 1 completely surrounds the axis of rotation A-A, the groove could partially surround the axis A-A if the separation vessel is not annular. Preferably, a substantial portion of the groove 18 has a constant radius of curvature about the axis of rotation A-A and is positioned at a maximum possible radial distance on the rotor 12. This shape ensures that substances separated in the separation vessel 28 undergo relatively constant centrifugal forces as they pass from an inlet portion to an outlet portion of the separation vessel 28.

As shown in FIG. 1, a bracket 26 is provided on a top surface of the rotor 12. The bracket 26 releasably holds an elutriation chamber 30 on the rotor 12 so that an outlet 32 of the elutriation chamber 30 is positioned closer to the axis of rotation A-A than an inlet 34 of the elutriation chamber 30. The bracket 26 preferably orients the elutriation chamber 30 on the rotor 12 with a longitudinal axis of the elutriation chamber 30 in a plane transverse to the rotor's axis of rotation A-A. In addition, the bracket 26 is preferably arranged to hold the elutriation chamber 30 on the rotor 12 with the elutriation chamber outlet 32 facing the axis of rotation A-A. Although the elutriation chamber 30 is shown on a top surface of the rotor 12, the elutriation chamber 30 could also be secured to the rotor 12 at alternate locations, such as beneath the top surface of the rotor 12.

Figure 2:
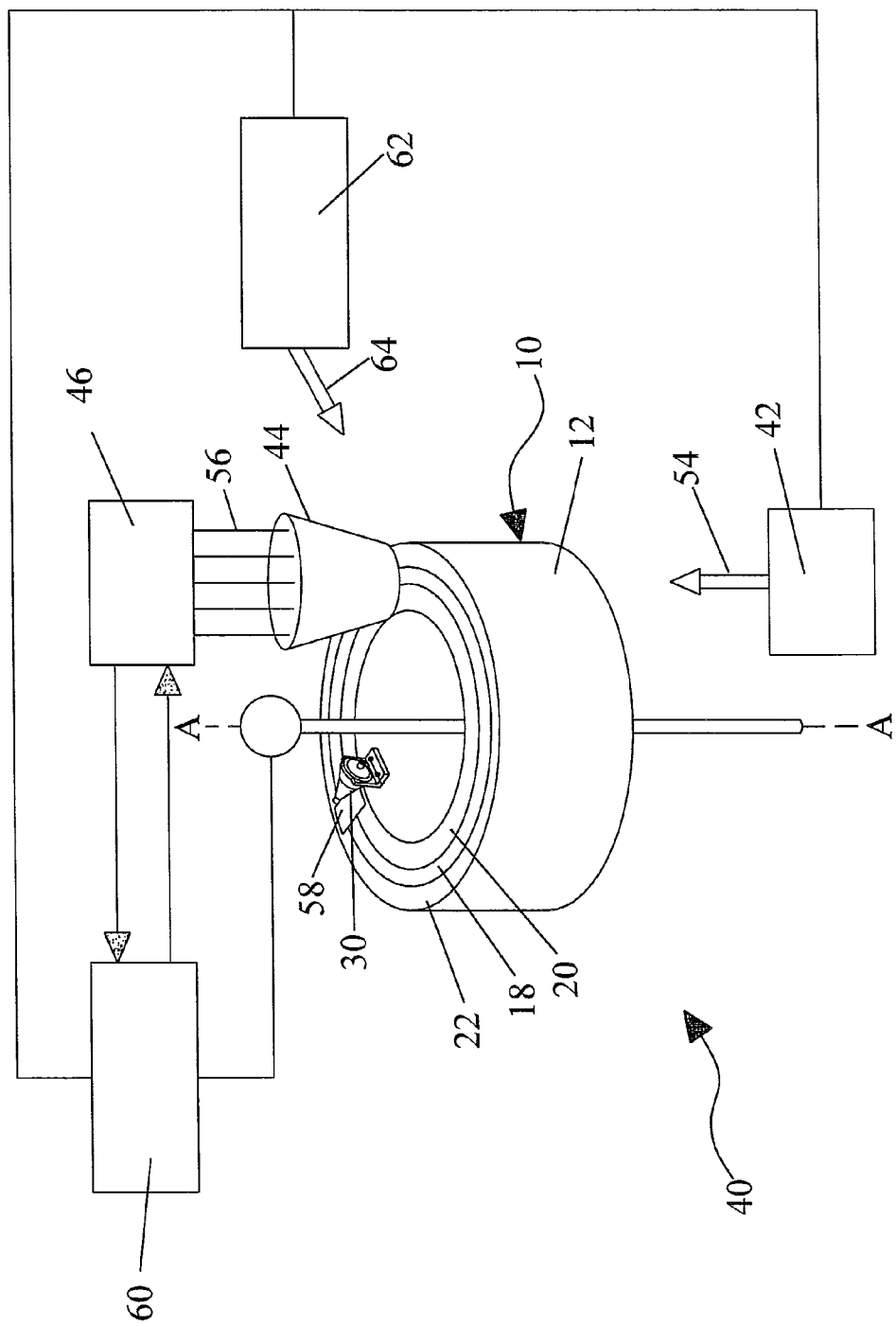
FIG. 2 is a schematic view of the centrifuge apparatus and a control camera.

FIG. 2 schematically illustrates an exemplary embodiment of an optical monitoring system 40 capable of detecting light coming from an observation region 58 on the separation vessel 28. The monitoring system 40 comprises light source 42, light collection element 44, and detector 46. Light source 42 is in optical communication with the centrifuge apparatus 10 and rotor 12. Rotation about central rotation axis A-A results in separation of a blood sample in the separation vessel 28 into discrete blood components.

Light source 42 provides incident light beam 54, which stroboscopically illuminates the observation region 58 when the observation region 58 passes under the light collection element 44. A portion of the incident light beam 54 is transmitted through at least one blood component undergoing separation in separation vessel 28. At least a portion of light 56 from the observation region 58 is collected by light collection element 44. Light collection element 44 is directs at least a portion of the collected light 56 onto detector 46. The detector 46 detects patterns of light 56 from the observation region 58. Optionally, the observation region 58 may also be illuminated by an upper light source 62, which is positioned on the same side of the separation chamber as the light collection element 44 and detector 46. Upper light source 62 is positioned such that it generates an incident beam 64, which is scattered by the blood sample and/or centrifuge. A portion of the light from upper light source 62 is collected by light collection element 44 and detected by detector 46. Detected light intensities comprise images or observations corresponding to patterns of light originating from the observation region 58. The images may be monochrome images, which provide a measurement of the brightness of separated blood components along separation axis. Alternatively, the images may be color images, which provide a measurement of the colors of separated blood components along the separation axis.

Figure 6:
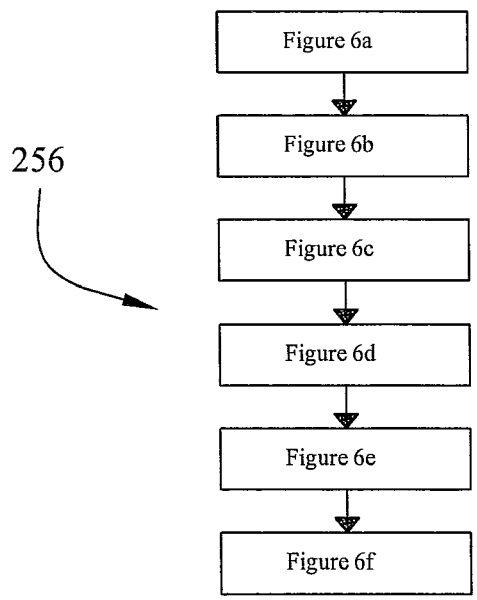
FIG. 6 is a representation of the relationship between FIG. 6a through FIG. 6f.
Figure 6A:
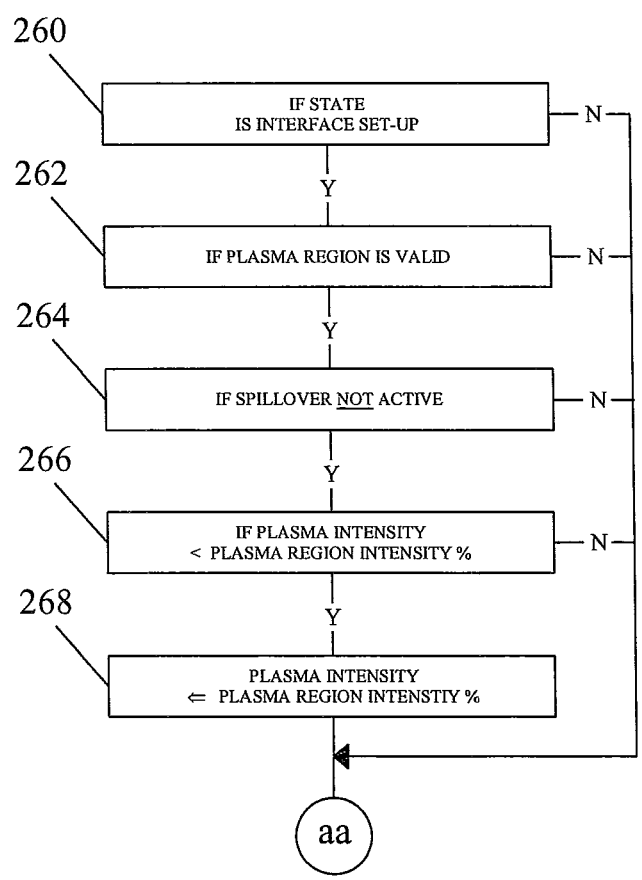
FIG. 6a through FIG. 6f are graphic representations of steps for image processing according to the present invention.
Figure 6B:
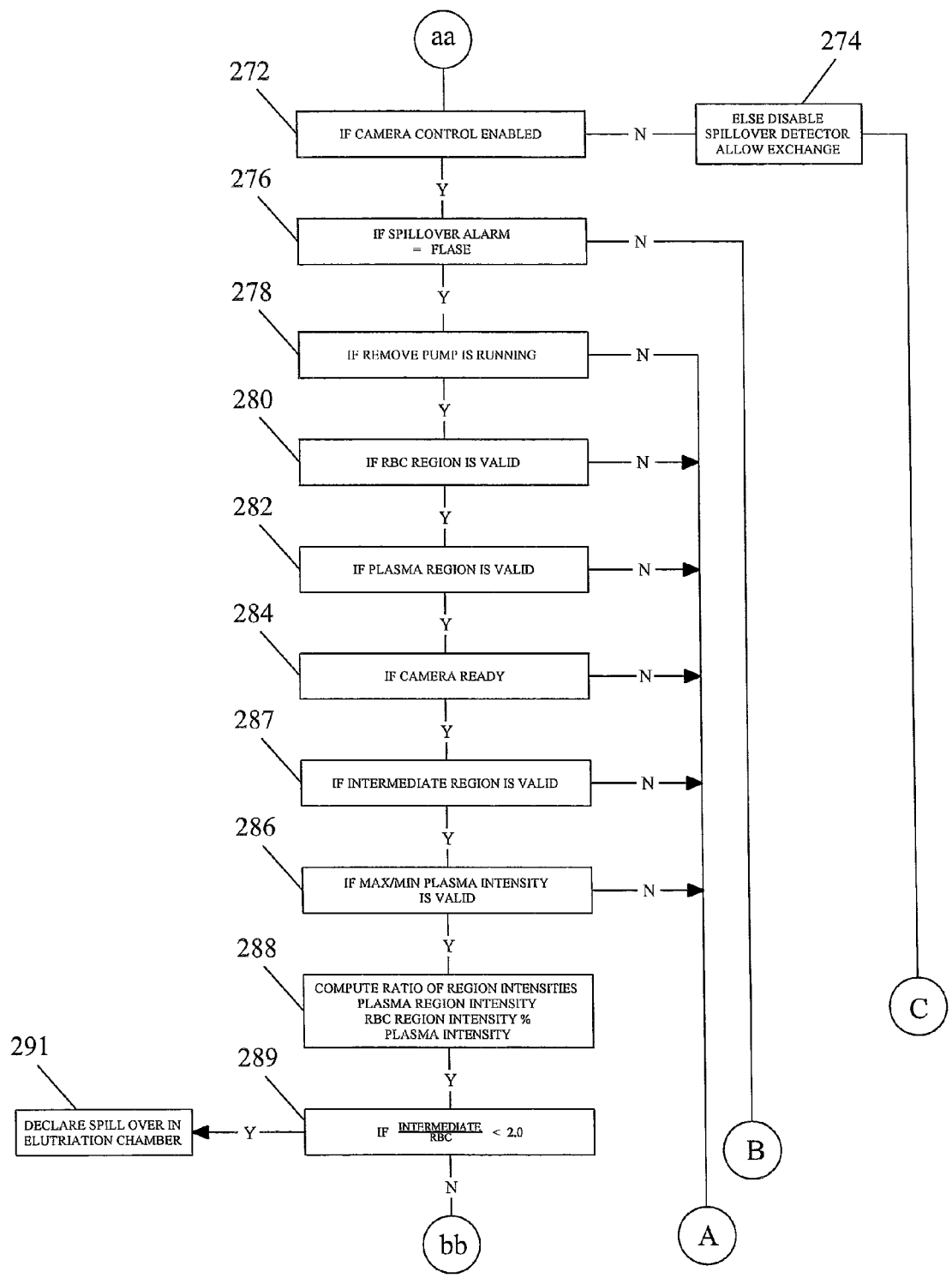
Figure 6C:
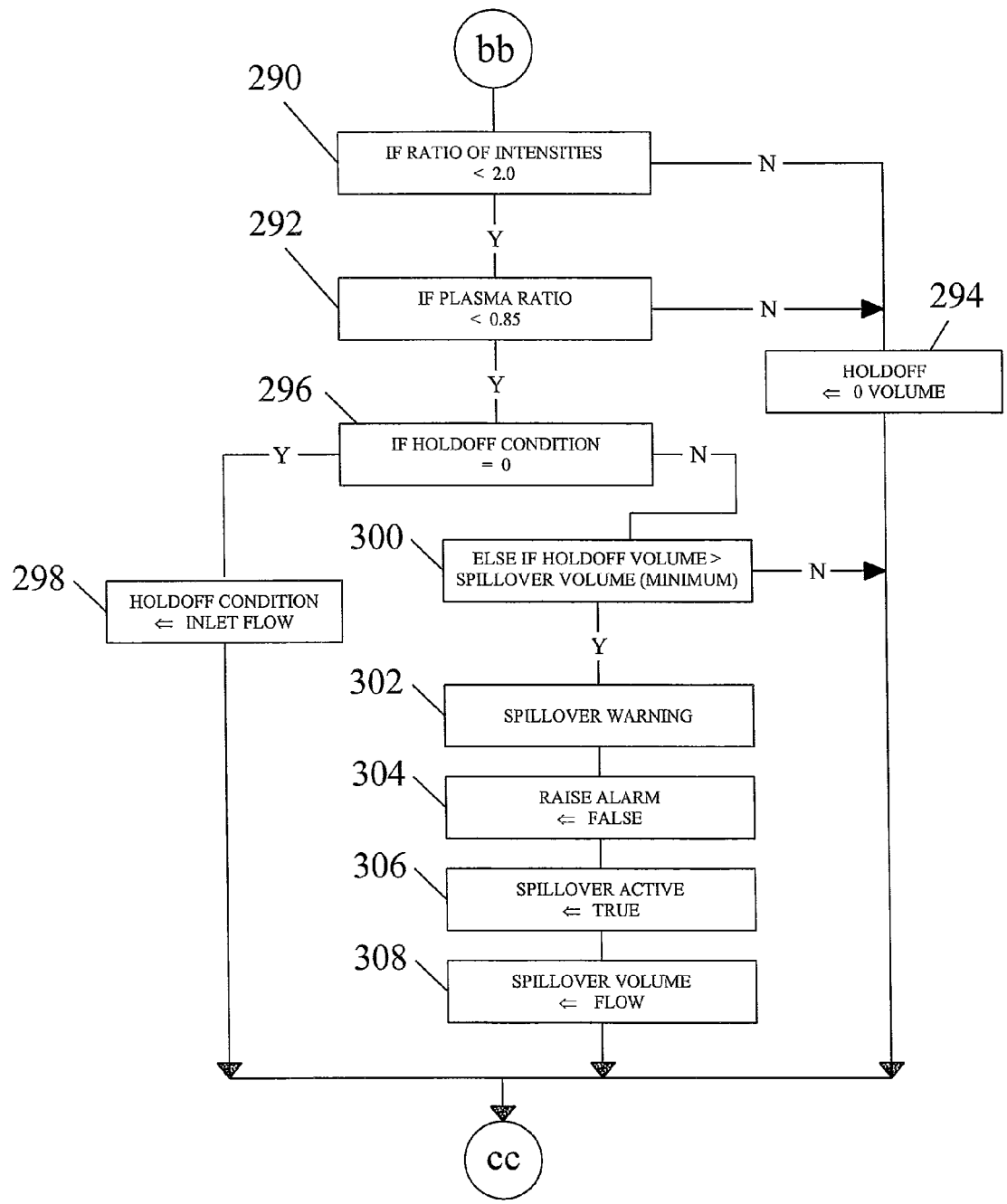
Figure 6D:
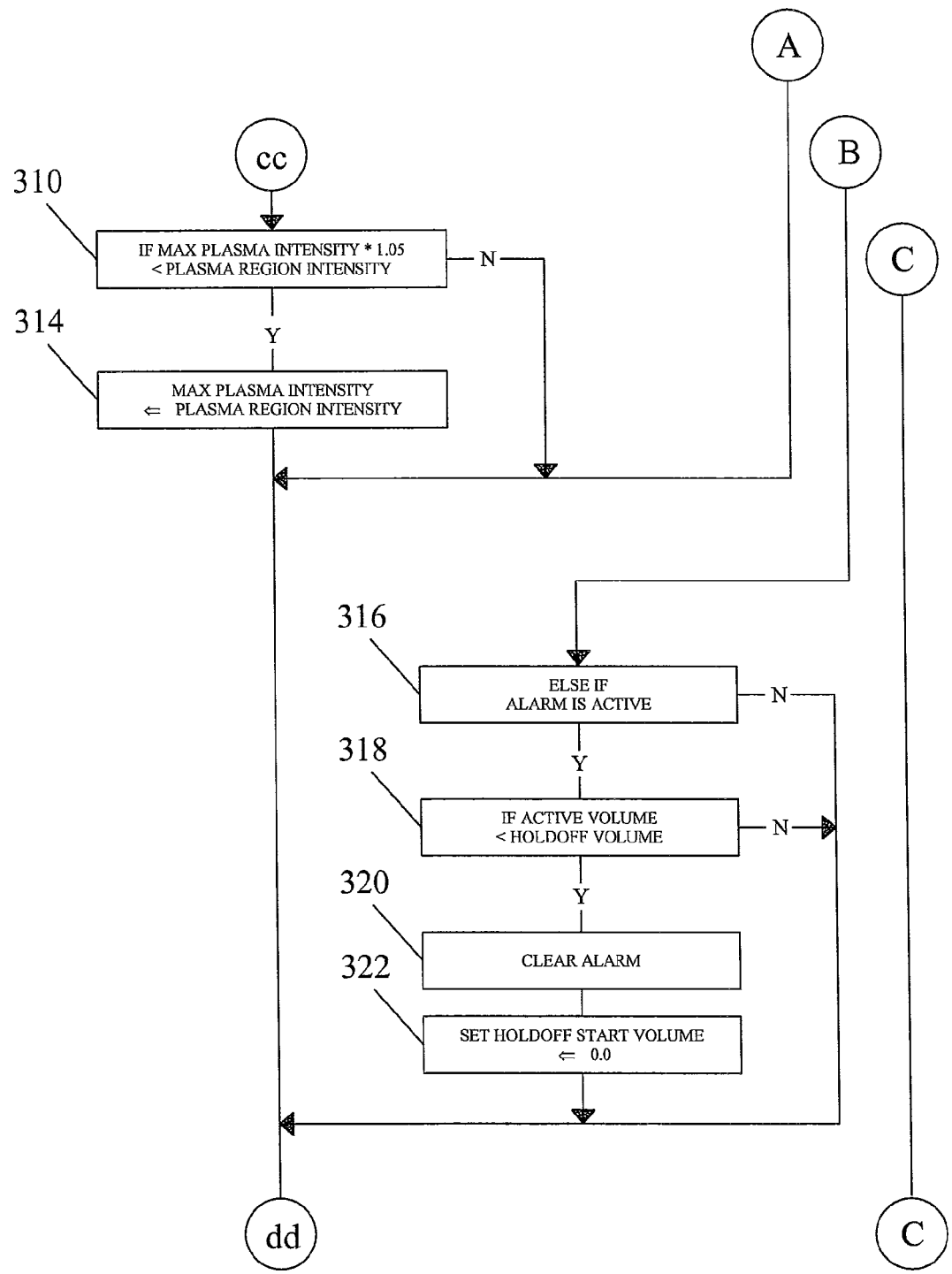
Figure 6E:
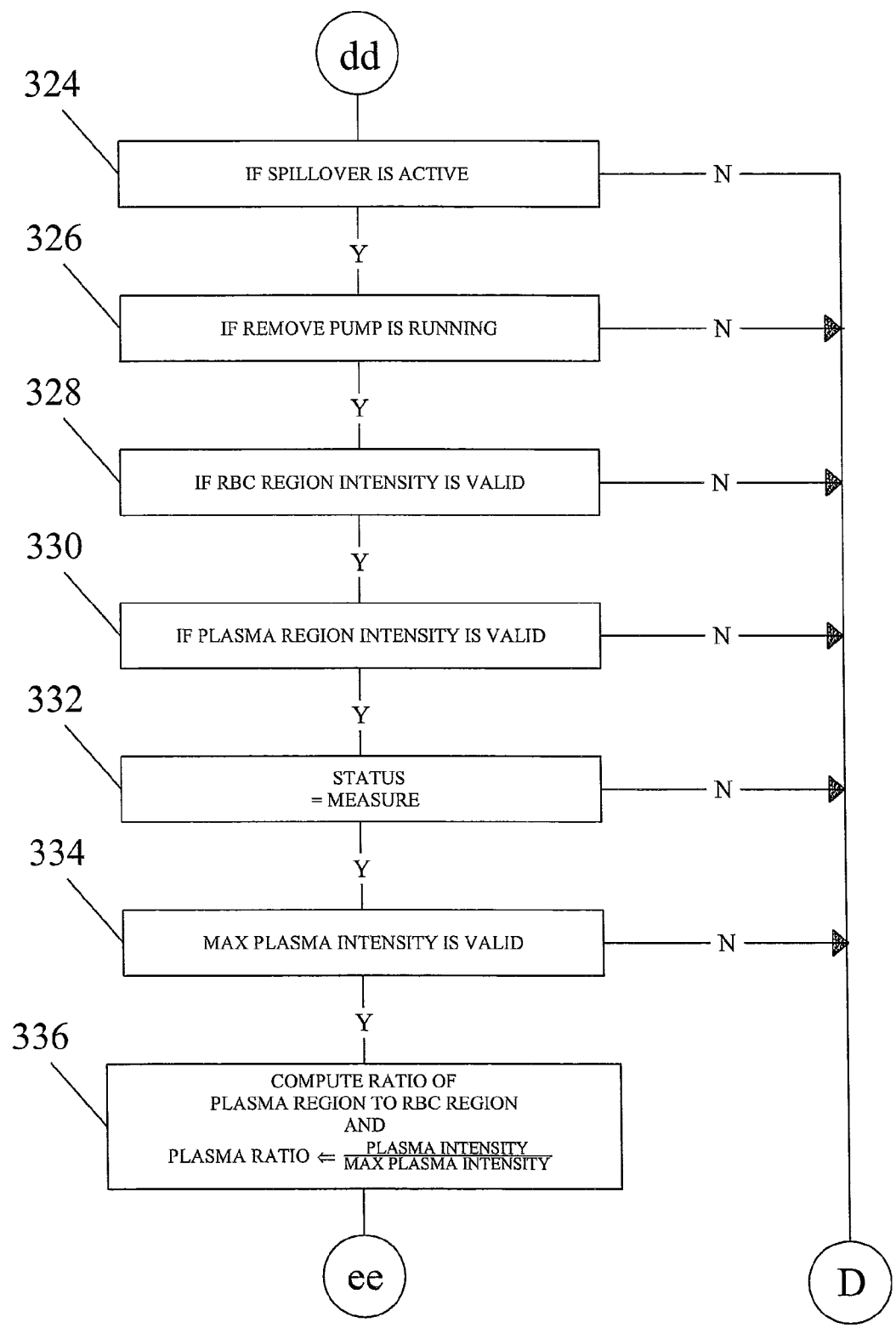
Figure 6F:
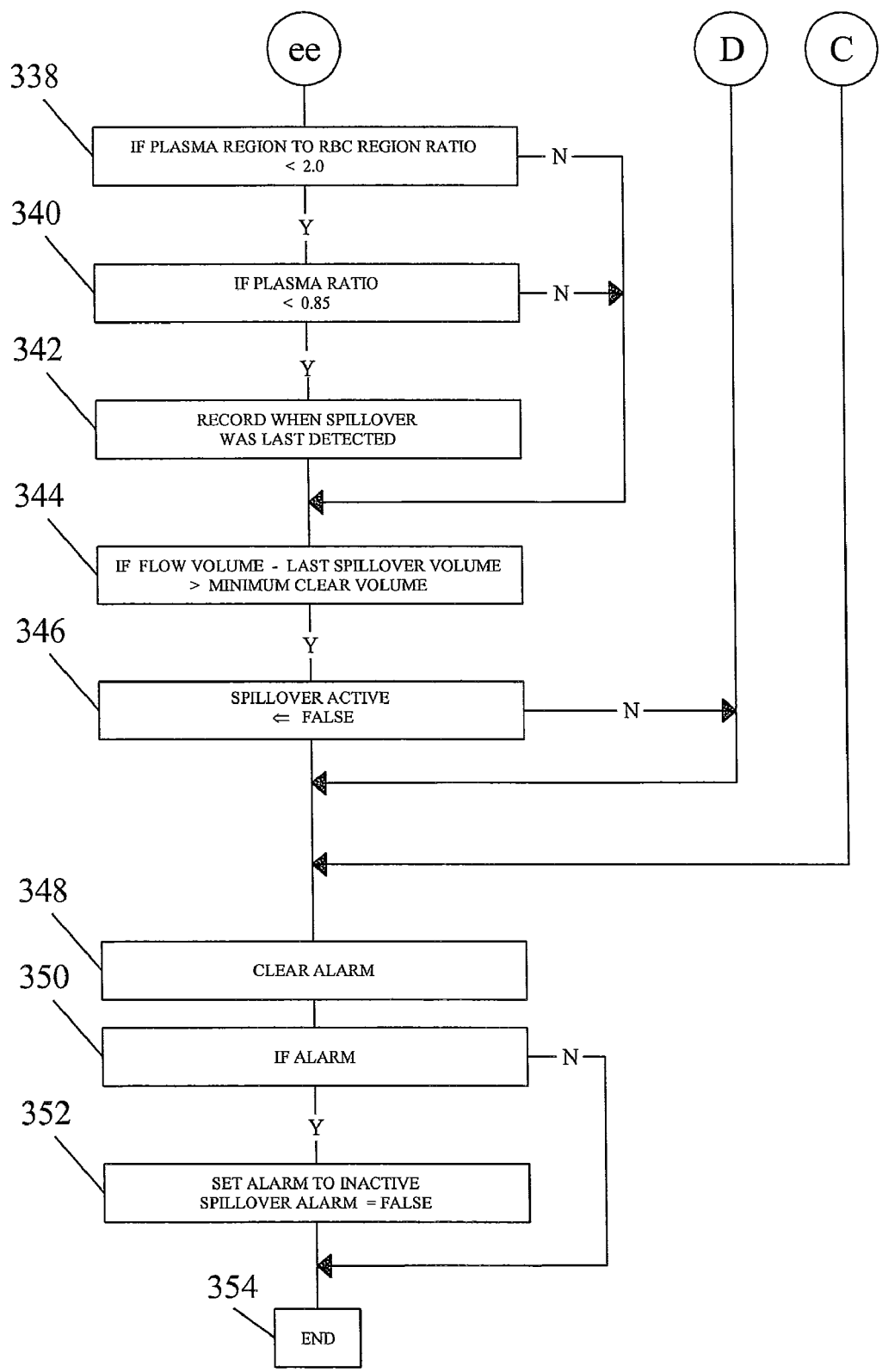

Observation region 58 is positioned on a portion of the density centrifuge 10, preferably on the separation vessel 28. The elutriation chamber 30 may also be an observation region. In the exemplary embodiment illustrated in FIG. 6, separated blood components and phase boundaries between optically differentiable blood components are viewable in observation region 58. Detector 46 also generates output signals corresponding to the images. The detector 46 is operationally connected to a device controller 60 capable of receiving the output signals. Device controller 60 displays the measured intensity distributions, stores the measured intensity distributions, processes measured intensity distributions in real time, transmits control signals to various optical and mechanical components of the monitoring system and centrifuge, or any combination of these. Device controller 60 is operationally connected to centrifuge apparatus 10 and is capable of adjusting selected operating conditions of the centrifuge apparatus, such as the flow rates of cellular and non-cellular components out of the separation vessel 28 or elutriation chamber 30, the position of one or more phase boundaries, rotational velocity of the rotor about central rotation axis A-A, the infusion of anticoagulation agents or other blood processing agents to the blood sample, or any combination of these.

Device controller 60 can also be operationally connected to light source 42 or upper light source 62. Device controller 60 or detector 46 are capable of generating output signals for controlling illumination conditions. For example, output signals from the detector 46 can be used to control the timing of illumination pulses, illumination intensities, the distribution of illumination wavelengths or position of light source 42 or of upper light source 62. Device controller 60 and detector 46 are in two-way communication, and the device controller sends control signals to detector 46 to selectively adjust detector exposure time, detector gain and to switch between monochrome and color imaging.

Light sources 42, 62 comprise light emitting diode sources capable of generating one or more incident beams for illuminating the observation region 58 on the centrifuge apparatus 10. A plurality of lamps may be positioned to illuminate a single side or multiple sides of the centrifuge apparatus 10. Light emitting diodes and arrays of light emitting diode light sources are preferred for some applications because they are capable of generating precisely timed illumination pulses. Preferred light sources generate an incident light beam having a substantially uniform intensity, and a selected wavelength range.

The optical monitoring system may comprise a plurality of light sources, each capable of generating an incident light beam having a different wavelength range, for example, a combination of any of the following: white light source, red light source, green light source, blue light source and infra red light source. Use of a combination of light sources having different wavelength ranges is beneficial for discriminating and characterizing separated blood fractions because absorption constants and scattering coefficients of cellular and non-cellular components of blood vary with wavelength. For example, a component containing red blood cells is easily distinguished from platelet-enriched plasma by illumination with light having wavelengths selected over the range of about 500 nm to about 600 nm, because the red blood cell component absorbs light over this wavelength significantly more strongly that the platelet-enriched plasma component. In addition, use of multiple colored light sources provides a means of characterizing the white blood cell type in an extracted blood component. As different white blood cell types have different absorption and scattering cross sections at different wavelengths, monitoring transmitted and/or scattered light from a white cell-containing blood component provides a means of distinguishing the various white blood cell types in a blood component and quantifying the abundance of each cell-type.

The light sources provide a continuous incident light beam or a pulsed incident light beam. Pulsed light sources are switched on and off synchronously with the rotation of the rotor to illuminate the observation region 58, which has a substantially fixed position on the rotor 12. Alternatively, pulsed light sources of the present invention can be configured such that they can be switched on and off at different angular positions, synchronous with the rotation of the rotor, illuminating different observation regions for each full rotation. This alternative embodiment provides a method of selectively adjusting the location of the observation region and, thereby, probing different regions of the separation chamber or of the elutriation chamber 30. Triggering of illumination pulses may be based on the rotational speed of the centrifuge or on the angular position of the separation chamber or the elutriation chamber 30 as detected by optical or electronic methods well known in the art. Triggering may be provided by trigger pulses generated by the device controller 60 and/or detector 46.

Figure 3:
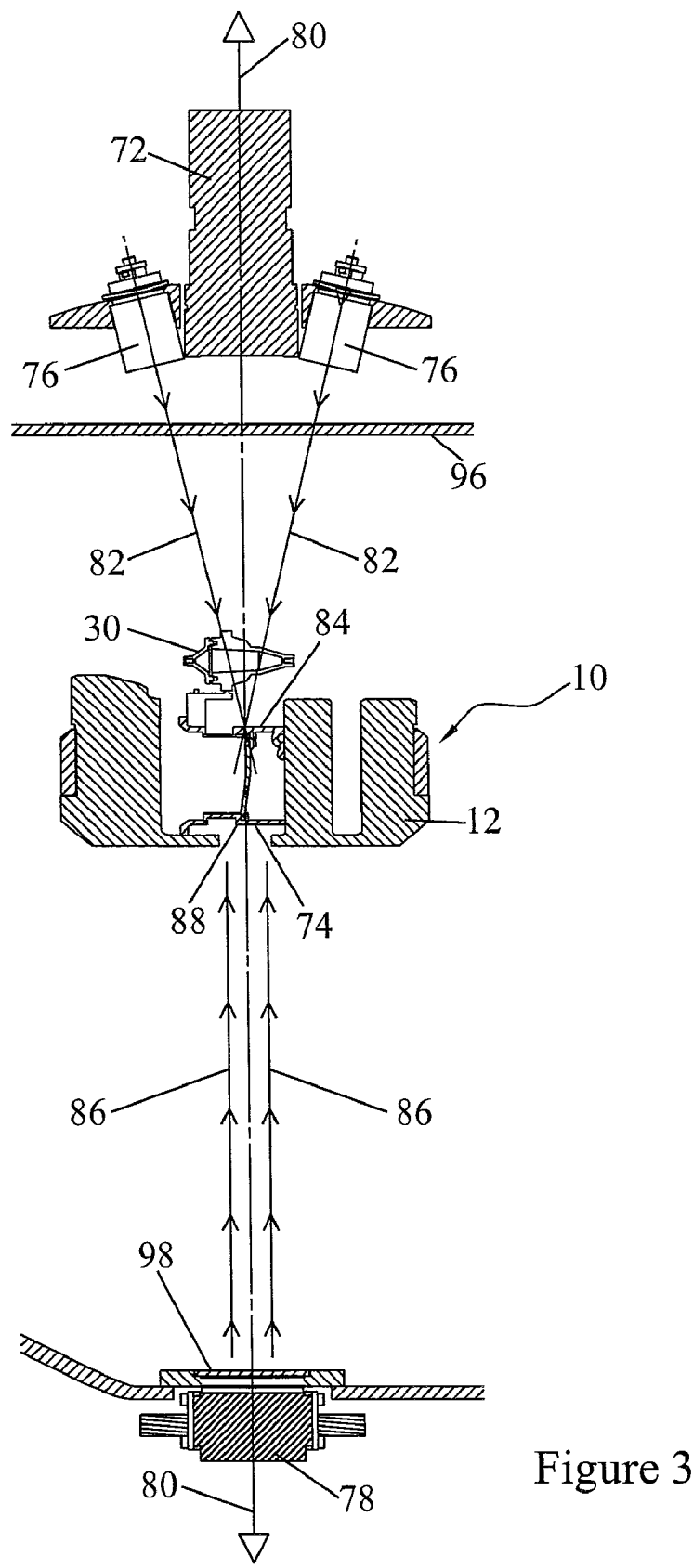
FIG. 3 is a partial cross-sectional view of blood processing apparatus of FIG. 2, including the elutriation chamber of FIG. 1.

FIG. 3 is a cutaway view corresponding to cutaway of the optical monitoring system 40. The illustrated optical monitoring system 40 comprises CCD (charge coupled device) camera 72 (CMOS (complementary metal oxide semiconductor) or other cameras could also be used) equipped with a fixed focus lens system (corresponding to the light collection element 44 and detector 46), an optical cell 74 (corresponding to the observation region 58), an upper LED light source 76 (corresponding to the upper light source 62), and a bottom pulsed LED light source 78 (corresponding to the light source 42). As illustrated in FIG. 3, CCD camera 72 is in optical communication with optical cell 74 and positioned to intersect optical axis 80. Upper LED light source 76 is in optical communication with optical cell 74 and is positioned such that it is capable of directing a plurality of collimated upper light beams 82, propagating along propagation axes that intersect optical axis 80, onto the top side 84 of optical cell 74. Bottom pulsed LED light source 78 is also in optical communication with optical cell 74 and is positioned such that it is capable of directing a plurality of collimated bottom light beams 86, propagating along optical axis 80, onto the bottom side 88 of optical cell 74.

CCD camera 72 may be positioned such that the focal plane of the fixed focus lens system is substantially co-planar with selected optical surfaces of optical cell 74, such as optical surfaces corresponding to an interface monitoring region, calibration markers, one or more extraction ports and one or more inlets. The CCD camera 72 is separated from the center of the fixed focus lens system by a distance along optical axis 80 such that an image corresponding to selected optical surfaces of optical cell 74 is provided on the sensing surface of the CCD camera. This optical configuration allows distributions of light intensities comprising images of rotating optical cell 74 or of elutriation chamber 30 to be measured and analyzed in real time.

Referring to FIG. 3, first transparent plate 96 is provided between CCD camera 72 and optical cell 74, and second transparent plate 98 is provided between bottom LED light source 78 and optical cell 74. First and second transparent plates 96 and 98 physically isolate CCD camera 72, upper LED light source 76 and bottom LED light source 78 from optical cell 74 so that these components will not contact a sample undergoing processing in the event of sample leakage from the separation chamber. In addition, first and second transparent plates 96 and 98 minimize degradation of CCD camera 72, upper LED light source 76 and bottom LED light source 78 due to unwanted deposition of dust and other contaminants that can be introduced to the system upon rotation of the separation chamber and filler. Further, first and second transparent plates 96 and 98 also allow a user to optimize the alignment of the camera, upper LED light source and bottom LED light source without exposure to a blood sample in the separation chamber. First and second transparent plates 96 and 98 can comprise any material capable of transmitting at least a portion of upper and bottom illumination light beams 82 and 86. Exemplary materials for first and second transparent plates 96 and 98 include, but are not limited to, glasses such as optical quality scratch resistant glass, transparent polymeric materials such as transparent plastics, quartz and inorganic salts.

Figure 4:
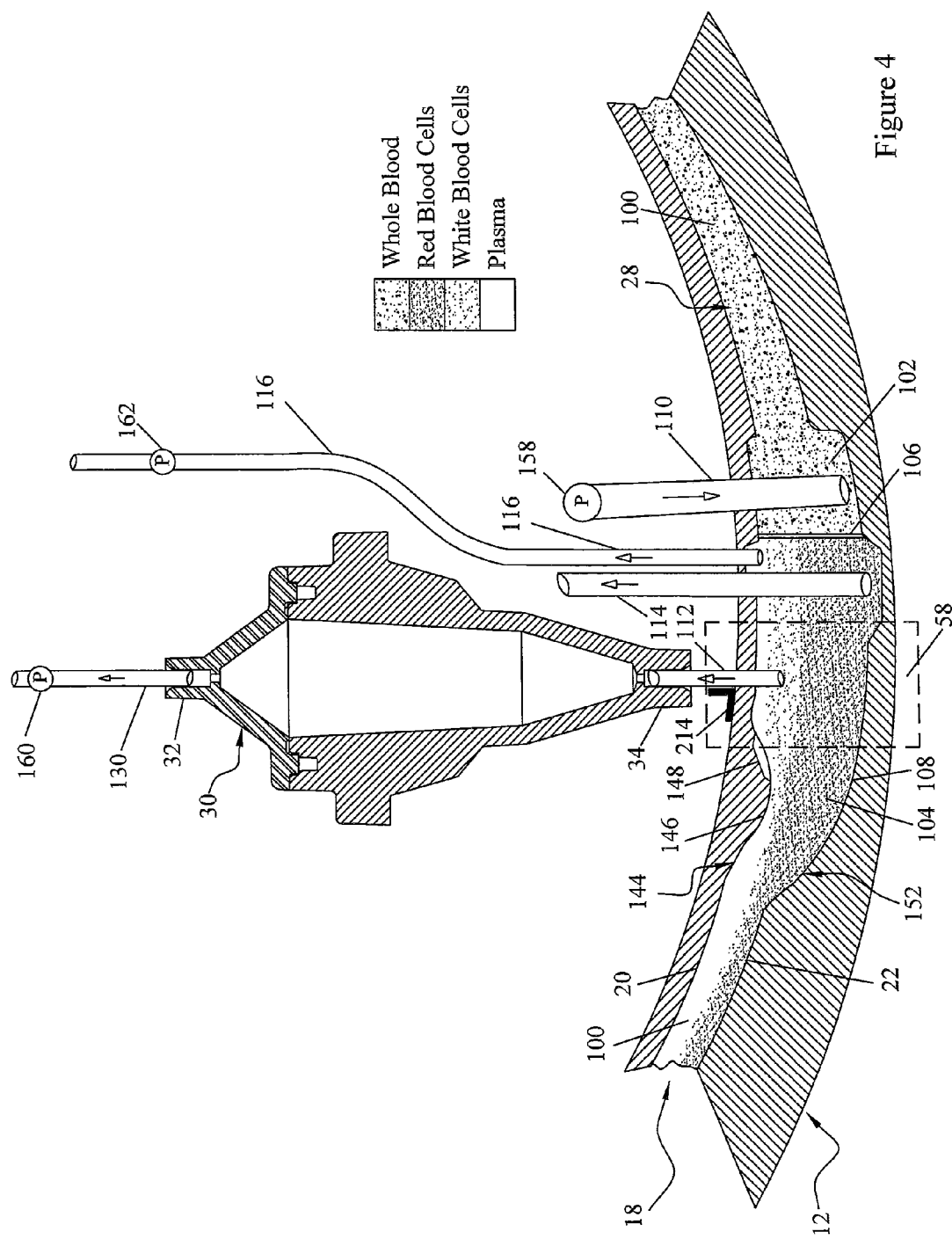
FIG. 4 is a partial cross-sectional, schematic view of a portion of a separation vessel and the elutriation chamber mounted on a centrifuge rotor of FIG. 1.

FIG. 4 schematically illustrates a portion of the separation vessel 28 and elutriation chamber 30 mounted on the rotor 12. The separation vessel 28 has a generally annular flow path 100 and includes an inlet portion 102 and outlet portion 104. A wall 106 prevents substances from passing directly between the inlet and outlet portions 102 and 104 without first flowing around the generally annular flow path 100 (e.g., counterclockwise in FIG. 4). A radial outer wall 108 of the separation vessel 28 is positioned closer to the axis of rotation A-A in the inlet portion 102 than in the outlet portion 104. During separation of blood components, this arrangement causes formation of a very thin and rapidly advancing red blood cell bed in the separation vessel 28 between the inlet portion 102 and outlet portion 104. The red blood cell bed reduces the amount of blood components required to initiate a separation procedure, and also decreases the number of unnecessary red blood cells in the separation vessel 28. The red blood cell bed substantially limits or prevents platelets from contacting the radial outer wall 108 of the separation vessel 28. This is believed to reduce clumping of platelets caused when platelets contact structural components of centrifugal separation devices.

The inlet portion 102 includes an inflow tube 110 for conveying a fluid to be separated, such as whole blood, into the separation vessel 28. During a separation procedure, substances entering the inlet portion 102 follow the flow path 100 and stratify according to differences in density in response to rotation of the rotor 12. The outlet portion 104 includes first, second, and third outlet lines 112, 114, 116 for removing separated substances from the separation vessel 28. Preferably, each of the components separated in the vessel 28 is collected and removed in only one area of the vessel 28, namely the outlet portion 104. In addition, the separation vessel 28 preferably includes a substantially constant radius except in the region of the outlet portion 104 where the outer wall of the outlet portion 104 is preferably positioned farther away from the axis of rotation A-A to allow for outlet ports of the lines 112, 114, and 116 to be positioned at different radial distances and to create a collection pool with greater depth for the high density red blood cells. The outlet port of line 114 is farther from the axis of rotation A-A than the other ports to remove higher density components, such as red blood cells. The port of line 116 is located closer to the axis of rotation A-A than the other ports to remove the least dense components separated in the separation vessel 28, such as plasma. The first line 112 collects intermediate density components and, optionally, some of the lower density components. The second and third lines 114 and 116 are positioned downstream from first line 112 to collect the high and low density components.

The positions of the interfaces are controlled by the CCD camera 72 monitoring the position of the interface and controlling flow of liquid and/or particles in response to the monitored position. Further details concerning the structure and operation of the separation vessel 28 are described in U.S. Pat. No. 7,422,693 and also in U.S. Pat. No. 4,094,461 to Kellogg et al. and U.S. Pat. No. 4,647,279 to Mulzet et al.

A ridge 144 extends from the inner wall 20 of the groove 18 toward the outer wall 22 of the groove 18. When the separation vessel 28 is loaded in the groove 18, the ridge 144 deforms semi-rigid or flexible material in the outlet portion 104 of the separation vessel 28 to form a trap dam 146 in the separation vessel 28, upstream from the first line 112. The trap dam 146 extends away from the axis of rotation A-A (see FIG. 1) to trap a portion of lower density substances, such as priming fluid and/or plasma, along an inner portion of the separation vessel 28 located upstream the trap dam 146. These trapped substances help convey platelets to the outlet portion 104 and first line 112 by increasing plasma flow velocities next to the layer of red blood cells in the separation vessel 28 to scrub platelets toward the outlet portion 104. A downstream portion 148 of the trap dam 146 has a relatively gradual slope extending in the downstream direction toward the axis of rotation A-A, which limits the number of platelets (intermediate density components) that become re-entrained (mixed) with plasma (lower density components) as plasma flows along the trap dam 146. In addition, the gradual slope of the downstream portion 148 reduces the number of platelets that accumulate in the separation vessel 28 before reaching the first collection port 120.

Figure 5:
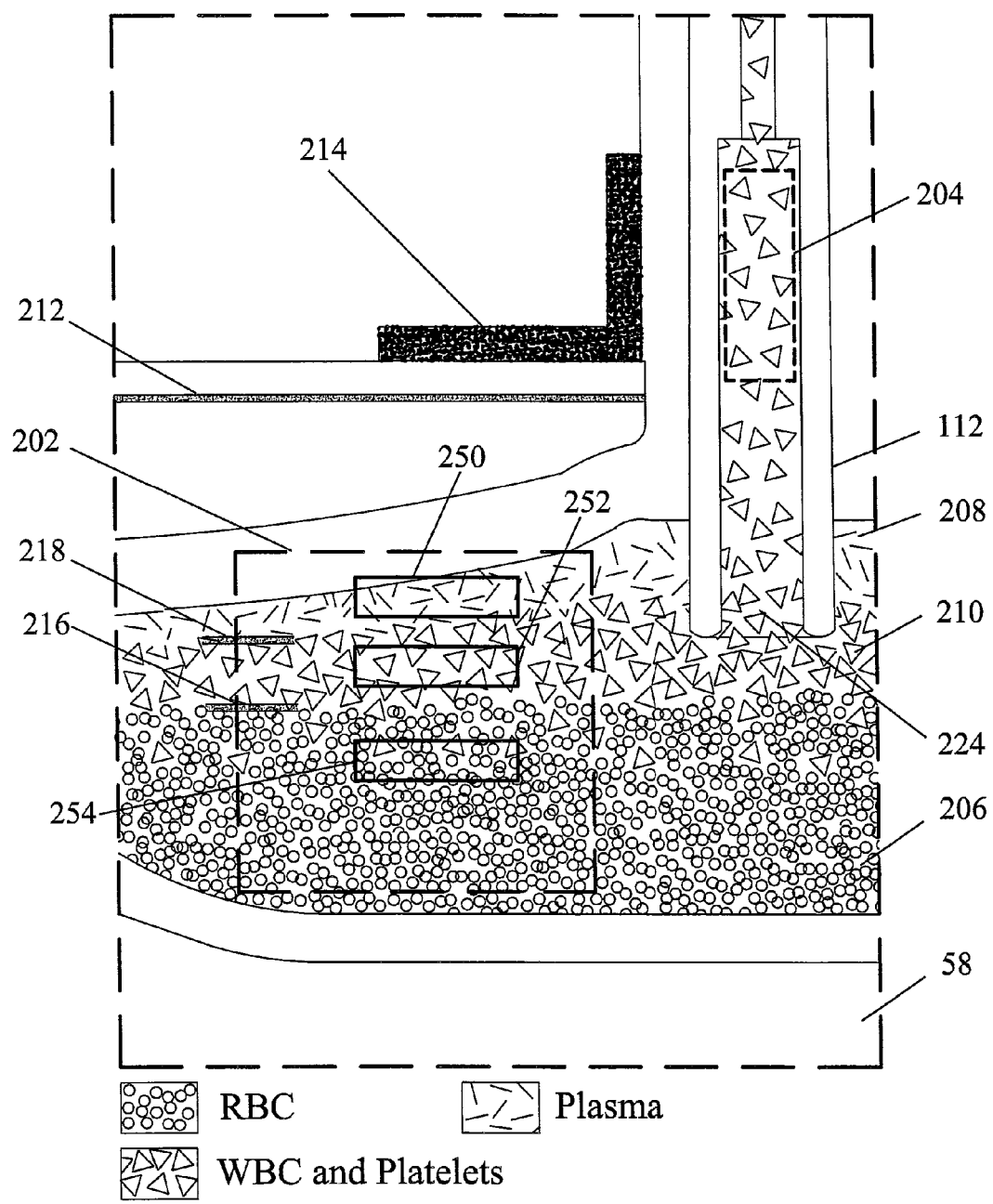
FIG. 5 is a plan view of a separation chamber of the separation vessel of FIG. 4.

The camera 44 is generally focused on the separation vessel and stroboscopic illumination allows the observation region 58 around the first, second, and third lines 112, 114, and 116 to be observed. Using information gathered through the camera, the controller 60 regulates the position of interfaces between various blood components, such as plasma, buffy coat (containing monocytes and/or white blood cells and platelets) and red blood cells by controlling the pumps 158, 160, and 162. FIG. 5 shows an image of the observation region 58 generated by the methods of U.S. Pat. No. 7,422,693. The observation region 58 shown in FIG. 5 includes a phase boundary monitoring region 202 and an extraction or collect port monitoring region 204, the extraction port being connected through the first line 112 to the elutriation chamber 30. Visible in phase boundary monitoring region 202 are a red blood cell component 206, a plasma component 208 and a mixed-phase buffy coat layer 210, which has both white blood cells and platelets. Several calibration markers are also apparent in the image in FIG. 5. Near an edge 212 of the optical cell is an L-shaped calibration marker or optical reference 214 for determining the absolute position of phase boundaries between optically differentiable blood components. The inner edge of the optical reference 214 is used to indicate the positions and physical dimensions of the phase boundary monitoring region 202 and the white blood cell collect port monitoring region 204. The physical dimension may be determined by adjusting the optics to within a selected range and then configuring the software with a parameter to convert pixels to microns. Alternatively, the thickness of the optical reference, usually about 1 mm, could be used. Light intensities transmitted through the phase boundary monitoring region 202 are acquired as a function of time and analyzed in real time to provide measurements of the position of the phase boundary 216 between red blood cell component 206 and buffy coat layer 210 and the phase boundary 218 between the buffy coat layer 210 and plasma component 208. All boundary layer positions are measured relative to the edge of the optical reference 214.

Collect port monitoring region 204 is used to monitor flow in first line 112 of the optical cell for extracting a blood component, for example, platelets or white blood cells. The apparatus responds to changes in detected blood component flow to establish a correct phase boundary level and further responds to changes in observed phase boundaries to maintain a consistent phase boundary level. The system discriminates between a plasma flow condition, a white blood cell flow condition, and a red blood cell flow condition, and can detect pump-induced flow variation in the blood component flow in said collect port measuring area. A plasma signal limit and a red blood cell signal limit may be set and the flow of fluid adjusted based on said limits. The system derives a statistical measure of fluid flow in the collect port measuring area, which may be a moving median of the average value of intensity of pixels in the collect port measuring area.

In this example, first line 112 having orifice 224 terminates proximate to the buffy coat layer in the rotating separation chamber. The light transmitted through the collect port in the collect port monitoring region 204 depends on the concentration, spatial distribution, and cell-type of cellular material exiting the separation chamber. Light intensities transmitted through the collect port monitoring region 204 are acquired as a function of time and analyzed to characterize the composition and flux of cellular material out of the separation chamber. As cellular materials, such as platelets, white blood cells and red blood cells, absorb and scatter light from the light sources 42, 64, passage of cellular material through the extraction port decreases the observed light intensities.

Referring again to FIG. 4, the outer wall 22 of the groove 18 preferably includes a gradual sloped portion 152 facing the ridge 144 in the inner wall 20. When the separation vessel 28 is loaded in the groove 18, the gradual sloped portion 152 deforms semi-rigid or flexible material in the outlet portion 104 of the separation vessel 28 to form a relatively smooth and gradual sloped segment in a region of the vessel 28 across from the trap dam 146, which slopes gradually away from the axis of rotation A-A to increase the thickness of a layer of high-density fluid components, such as red blood cells, formed across from the trap dam 146.

The first collection line 112 is connected to the elutriation chamber inlet 34 to pass the intermediate density components into the elutriation chamber 30. Components initially separated in the separation vessel 28 are further separated in the elutriation chamber 30. For example, white blood cells and platelets could be separated from plasma in the elutriation chamber 30. This further separation preferably takes place by forming a saturated fluidized bed of particles, such as platelets and white blood cells, in the elutriation chamber 30. The elutriation chamber 30 may be formed of a transparent or translucent co-polyester plastic, such as PETG, to allow viewing of the contents within the chamber interior with the aid of the camera during a separation procedure.

As schematically shown in FIG. 4, a plurality of pumps 158, 160, and 162 are provided for adding and removing substances to and from the separation vessel 28 and elutriation chamber 30. An inflow pump 158 is coupled to the inflow line 110 to supply the substance to be separated, such as whole blood, to the inlet portion 102. In addition, a first collection pump 160 is flow coupled to the outflow tubing 130 connected to the elutriation chamber outlet 32, and a second collection pump 162 is flow coupled to the third collection line 116. The first collection pump 160 draws liquid and particles from the elutriation chamber outlet 32 and causes liquid and particles to enter the elutriation chamber 30 via the elutriation chamber inlet 34. The second collection pump 162, on the other hand, removes primarily low-density substances, such as plasma, from the separation vessel 28 via the third line 116.

The pumps 158, 160, and 162 are peristaltic pumps or impeller pumps configured to prevent significant damage to blood components. However, any fluid pumping or drawing device may be provided. In an alternative embodiment (not shown), the first collection pump 160 may be fluidly connected to the elutriation chamber inlet 34 to directly move substances into and through the elutriation chamber 30. In addition, the pumps 158, 160, and 162 may be mounted at any convenient location. The inflow pump 150 and the first collection pump 160 may be configured so that substances do not bypass these pumps when they are paused. For example, when the first collection pump 160 is temporarily paused, substances pumped by the second collection pump 162 flow into the elutriation chamber outlet 32 rather than bypassing the pump 160 and flowing in the opposite direction.

The controller 60 (FIG. 1) is connected to the motor 14 to the rotor 12 and the pumps 158, 160, and 162 to control the flow rate of substances flowing to and from the separation vessel 28 and the elutriation chamber 30. The controller 60 controls the operation and flow rate of the pumps 158, 160, 162 to permit the temporary purging of the elutriation chamber 30. The controller 60 may include a computer having programmed instructions provided by a ROM or RAM as is commonly known in the art.

In the outlet portion 104, platelet poor plasma flows through the third line 116. These relatively low-density substances are pumped by the second collection pump 162 through the third collection line 116. Red blood cells are removed via the second line 114. The red blood cells flow through the second collection line 114 and can then be collected and optionally recombined with other blood components or further separated. Alternately, these removed blood components may be re-infused into a donor or patient.

Accumulated platelets are removed via the first collection line 112 along with some of the white blood cells and plasma. As the platelets, plasma, white blood cells, and possibly a small number of red blood cells pass through the first collection line 112, these components flow into the elutriation chamber 30, filled with the priming fluid, so that a saturated fluidized particle bed may be formed. The platelets flow toward the first collection line 112.

The controller 60 maintains the rotation speed of the rotor 12 within a predetermined rotational speed range to facilitate formation of this saturated fluidized bed. In addition, the controller 60 regulates the pump 160 to convey at least the plasma, platelets, and white blood cells at a predetermined flow rate through the first collection line 112 and into the inlet 34 of the elutriation chamber 30. These flowing blood components displace the priming fluid from the elutriation chamber 30. When the platelet and white blood cell particles enter the elutriation chamber 30, they are subjected to two opposing forces. Plasma flowing through the elutriation chamber 30 with the aid of pump 160 establishes a first viscous drag force that urges the particles toward the outlet 32. Centrifugal force created by rotation of the rotor 12 and elutriation chamber 30 acts to urge the particles toward the inlet 34.

The controller 60 regulates the rotational speed of the rotor 12 and the flow rate of the pump 160 to collect platelets and white blood cells in the elutriation chamber 30. In a high-speed centrifuge for separating blood components, control of the interface between blood components presents significant control problems. After steady state conditions have been established, the present apparatus controls the interface location by measuring light intensity in the collect port monitoring region 204 in the collect port by detecting the presence or absence of RBC's in the collect port, and by monitoring the interface 216 or 218 in the phase boundary or interface monitoring region 202. The light intensity in the collect port can be measured by both an average value over a relatively brief period of time or by a median value over a longer period of time or by a combination of both measurements. However, the present apparatus also continues to monitor the separation chamber or phase boundary monitoring region 202 to detect conditions that indicate potential or incipient spill over of red blood cells into the elutriation chamber 30. More importantly, the present apparatus monitors the separation chamber to detect incipient spill over of platelets or white blood cells into the outflow line 116, through which plasma is usually collected. In prior systems, white blood cells, platelets or red blood cells entering the outflow line 116 have been detected by red-green optical sensors mounted on the apparatus, but off of the rotor 12. Thus, these cells have usually advanced a significant distance into the outflow line 116 before they are detected, and may, therefore, enter the plasma collection bag. It is desirable to avoid such a condition.

The improved detection algorithm disclosed herein identifies three discrete regions within the phase boundary monitoring region 202 and compares intensities within these regions to anticipate spill over, that is, flow of an undesired blood component into the outflow tubes 116 or 112. The three regions are relatively small compared to the total phase boundary monitoring region 202. Preferably, the regions are spaced apart from each other and comprise a plasma region 250, an intermediate region 252 and a red blood cell region 254. The plasma region 250 and the red blood cell region 254 are monitored to prevent spill over into the plasma outflow tube 116. The intermediate region 252 is monitored to prevent spillover into the elutriation chamber. The algorithm compares the light intensity in the red blood cell region 254 to the light intensity in the plasma region 250. If the ratio of the plasma region intensity to the red blood cell region intensity exceeds 2.0, it is concluded that the blood components are sufficiently separated for further processing and plasma, for instance, may be extracted through the outlet port 112. The apparatus is then "armed", that is, in a state of testing for possible spill over. The maximum optical intensity in the plasma region 250 is detected. This condition is likely to occur when the ratio of plasma region intensity to red blood cell region intensity has exceeded 2.0. If the plasma intensity in the plasma region 250 decreases to a predetermined level of the maximum observed optical intensity in the plasma region 250, it is determined that spill over is likely to occur and flow rate or centrifuge speed or both may be changed to prevent spill over. Preferably, if the plasma region intensity divided by the maximum plasma intensity falls below 0.85 times the maximum intensity in the plasma region 250, a condition of incipient spill over is declared. The intermediate region 252 is also monitored. The intermediate region 252 usually falls within the white blood cell or buffy coat region. A decrease in optical intensity in the intermediate region indicates a rising red blood cell interface, which implies a possible spill over into the outflow tube 112. Therefore, decreasing optical intensity in the intermediate region is used as a back-up or fail safe test in addition to the comparison of the intensities of the plasma region 250 and the red blood cell region 254.

An algorithm 256 implementing incipient spill over detection is illustrated in FIGS. 6 and 6a through 6f. In broad outline, the algorithm confirms that implementing a detection test is appropriate, that is, that the apparatus is in a state wherein spill over could occur. The algorithm then tests for conditions indicative of potential spill over, and for such conditions to be sufficiently sustained to avoid a false positive test result. If sustained conditions indicating spill over exist, the operator is notified or corrective alteration of apparatus operating characteristics may be taken. The apparatus maintains this status until the indicating conditions have stopped for a pre-determined length of time.

To confirm that the spill over detection test can run, the apparatus tests that the apparatus has started interface setup 260, that is, for the condition that the apparatus is imitating a blood component interface in the separation chamber. The apparatus then determines if the optical intensity in the plasma region 250 can be measured by checking that the plasma region intensity reading must be valid 262, meaning that the observed intensity in the plasma region 250 must exceed a predetermined value. Finally, a spillover condition must not be currently detected 264. If these three conditions are met, a maximum plasma intensity can be recorded from plasma region 250. If the last recorded maximum plasma intensity is less 266 than the current intensity observed in the plasma region 250, then the recorded maximum plasma intensity is set 268 to the value of the currently observed intensity.

The algorithm then checks 272 if the camera is enabled. If camera control is not active, the processing will be controlled manually by an operator, and not automatically. The spillover detector would thereupon be disabled 274, and processing of the blood would be allowed under operator control. If the camera is found to be active 272, other conditions will be met for further automatic processing. The algorithm checks 276 that the spillover alarm has been cleared 276; that the fluid removal pump is running 278; that the observed intensity in the RBC region has an identifiable value 280, for example a value greater than a predetermined minimum, and that the plasma region also has at least a predetermined value 282, thereby indicating that valid signals from the two regions are being received. The readiness of the camera, per se, is confirmed 284. The maximum plasma intensity is validated 286, in other words, a positive reading has been obtained. Next, the intermediate region 252 is validated 287, that is a positive reading has been obtained. If these conditions are met, the ratio of the intensity of the plasma region 250 to the intensity of the red blood cell region 254 is computed 288. This is used to detect spill over into the plasma outflow tube 116. Next, the ratio of the intensity of the intermediate region 252 to the intensity of the red blood cell region 254 is computed 289 and compared to a preselected value, for example 2.0. If this condition is met, a spillover into the elutriation chamber 30 is declared 291. The pump 160 can be stopped to prevent additional fluid from entering the elutriation chamber. Otherwise, the algorithm proceeds for monitoring spill over into the plasma outlet line 116.

If the computed ratio of intensities of the plasma region 250 to the red blood cell region has fallen 290 below a predetermined spillover minimum level, and a plasma ratio (computed from the intensity of the plasma region 250 divided by the maximum plasma intensity obtained in step 268) is less than 0.85, it is possible that a spillover may be imminent. However, such a condition must persist for a length of time or volume of fluid flow before either a warning is given or pre-emptive corrective action is taken. If the ratio is high, there is a distinct difference between the plasma region and the red blood cell region, implying that separation between the two regions is distinct and red blood cells are unlikely to enter the plasma region. For a high ratio, a holdoff condition is set to zero 294. The holdoff condition represents the duration that a low ratio must be sustained before a spillover condition is confirmed. It may be measured, as here, by volume of fluid passing through the separation chamber (and thus be dependent on the rate of flow) or by elapsed time, or another suitable parameter. Resetting the holdoff condition to zero occurs whenever the spillover condition is no longer detected.

If the conditions for incipient spillover are detected 290, 292, and the holdoff condition is zero 296, meaning that a new incident has been detected, the holdoff condition is set 298 to the current inlet flow. As the control computer loops through the algorithm, subsequent tests increment the holdoff volume until it is greater than a minimum spillover volume 300, indicating that spillover conditions are stable. A spillover warning is issued 302 either to the control computer or the operator or both. Adjustments to operating conditions may then be made automatically or manually. After the warning has been given, an alarm flag may be reset 304 to "false", in preparation for a subsequent spillover detection test. A spillover active flag is set 306 to "true", allowing the algorithm to test, as described below, for a stable end of spillover conditions, analogous to the test for stable beginning of spillover conditions described above. A spillover volume is recorded 308 corresponding to the flow state of the apparatus. This would allow one to determine when the incipient spillover condition had occurred in the process.

The tests described herein are based on detection of variation from previous conditions. The apparatus, therefore, tests against a highest optical intensity detected in, for example, the plasma region 250. If the recorded plasma region intensity times a scaling factor (for example, 1.05) is less than the currently detected plasma region intensity (step 310), a new maximum plasma intensity will be set 314 using the current plasma region 250 intensity, thus establishing a new intensity maximum for future comparisons.

In parallel with the process described above, if it was determined in preliminary step 276 that the spillover alarm flag was true, the algorithm also tests that an alarm is being given 316 to the control computer or the operator or both until a predetermined holdoff volume of fluid has passed 318 through the separation chamber. If the alarm has been give for this duration, the alarm is cleared 320 and the holdoff volume is reset 322 to zero. This allows the apparatus to wait until an additional volume of blood has been processed before allowing an alarm to occur again.

After an incipient spillover condition has been detected, as described above, the apparatus now maintains a warning status until all the conditions have been reversed for a sufficient duration. Just as transient changes in certain parameters were rejected in recognizing incipient spillover conditions, so also transient reversion to previous conditions will not nullify a warning of potential spillover. If, therefore, a spillover flag is active 324, the algorithm tests whether the spillover conditions still exist. A volume of fluid must be flowing 326 through the remove pump 162 (FIG. 4). The apparatus must be detecting 328 a valid optical intensity in the RBC region 254, for example, greater than 0.1 percent absolute intensity, where 100 percent represents pure white and 0 percent represents pure black. Similarly, a valid optical intensity must be detected 330 in the plasma region 250. The functional status of the apparatus should be in an appropriate mode 332, for example, a measure mode wherein the camera is actively sensing the separation chamber. The maximum plasma intensity as obtained in step 314 should also be valid 334, for example, above 0.1 percent absolute intensity. If these conditions are met, the apparatus computes 336 the ratio of the intensity of the plasma region 250 to the intensity of the RBC region 254. If the plasma region intensity compared to the RBC region intensity ratio remains below a minimum intensity threshold 338, for example, below a threshold of 2.0, and if the plasma ratio remains below a minimum plasma intensity 340, for example, below a threshold of 0.85, the apparatus will record the current or last occurrence of spillover conditions 342 (called last spillover flow volume), in terms of elapsed flow volume, or elapsed time since the beginning of the spillover conditions, or other suitable benchmark. This testing continues until the flow volume (or other measure of duration) minus the last spillover flow volume is greater than 344 a minimum clear volume, that is, that non-spillover conditions have existed for a sufficient duration. A flag indicating the presence of incipient spillover conditions is then set 346 to "false".

The alarm flags may then be cleared 348, and, if it is determined 350 that an alarm is being sent to the controller or to an operator, the alarm will be turned off 352 and the spillover alarm flag set to "false." The algorithm ends 354 by returning control to other programs of the system. The controller implements the algorithm described above as part of a cyclic process which continuously monitors and controls the blood processing system. The particular features described herein allow the operator or the controller to be notified of the existence of conditions indicating that spillover of red blood cells into the plasma products being withdrawn from the separation chamber is eminent, but has not yet occurred. In response to an alarm, manual or automatic adjustments to system parameters, such as fluid flow rates or centrifuge speeds, whereby actual spillover of red blood cells or over components into plasma or other component collection bags can be avoided.

It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A method separating fluid components comprising:
    rotating a separation chamber about a central rotation axis;
    flowing fluid components out of said separation chamber;
    regulating fluid flow in said separation chamber using at least one pump;
    passing light through said separation chamber;
    detecting an intensity of light from at least two regions in said separation chamber;
    comparing said intensities in said at least two regions;
    distinguishing incipient spill over changes in fluid flow in said separation chamber as a function of said intensities of transmitted light received from said at least two regions;
    regulating the speed of said at least one pump or the speed of said separation chamber in response to signals from a computational apparatus to avoid spill over of cellular components from said separation chamber;

wherein said regions comprise a plasma region and a red blood cell region, said regions being placed such that, under normal circumstances, said plasma region observes primarily plasma and said red blood cell region observes primarily red blood cells;

computing a first intensity ratio of intensity of said plasma region to intensity of said red blood cell region; and declaring a state of testing for possible spill over whenever said first intensity ratio exceeds a pre-determined value.

2. The method of claim 1 further comprising recording a maximum plasma intensity and computing a second intensity ratio of said plasma region to the maximum recorded plasma intensity.

3. The method of claim 2 further comprising declaring a condition of incipient spill over whenever said second intensity ratio falls below a pre-determined portion of said maximum plasma intensity.

4. The method of claim 3 further comprising recording said maximum plasma intensity only after said state of testing for possible spill over has been declared.

5. The method of claim 4 further comprising detecting intensity of light from at least a third region comprising a buffy coat region, said buffy coat region being placed such that, under normal circumstances, said buffy coat region observes buffy coat.

6. The method of claim 5 wherein further comprising declaring a condition of incipient spill over whenever said intensity from said buffy coat region falls by a predetermined amount.

7. The method of claim 6 wherein said predetermined amount comprises a fraction of a maximum observed intensity in said buffy coat region.

8. A method separating fluid components comprising:
rotating a separation chamber about a central rotation axis;
flowing fluid components out of said separation chamber;
regulating fluid flow in said separation chamber using at least one pump;
passing light through said separation chamber;
detecting an intensity of light from at least two regions in said separation chamber;
comparing said intensities in said at least two regions;
distinguishing incipient spill over changes in fluid flow in said separation chamber as a function of said intensities of transmitted light received from said at least two regions;
regulating the speed of said at least one pump or the speed of said separation chamber in response to signals from a computational apparatus to avoid spill over of cellular components from said separation chamber;
wherein said regions comprise a plasma region and a red blood cell region, said regions being placed such that, under normal circumstances, said plasma region observes primarily plasma and said red blood cell region observes primarily red blood cells;
recording a maximum plasma intensity and computing a first intensity ratio of said plasma region to the maximum recorded plasma intensity; and
declaring a condition of incipient spill over whenever said first intensity ratio falls below a pre-determined portion of said maximum plasma intensity.

9. The method of claim 8 further comprising computing a second intensity ratio of intensity of said plasma region to intensity of said red blood cell region.

10. The method of claim 9 further comprising declaring a state of testing for possible spill over whenever said second intensity ratio exceeds a pre-determined value.

11. The method of claim 10 further comprising recording said maximum plasma intensity only after said state of testing for possible spill over has been declared.

12. The method of claim 11 further comprising detecting intensity of light from at least a third region comprising a buffy coat region, said buffy coat region being placed such that, under normal circumstances, said buffy coat region observes buffy coat.

13. The method of claim 12 wherein further comprising declaring a condition of incipient spill over whenever said intensity from said buffy coat region falls by a predetermined amount.

14. The method of claim 13 wherein said predetermined amount comprises a fraction of a maximum observed intensity in said buffy coat region.

* * * * *